US009562843B2

(12) United States Patent
Kim et al.

(10) Patent No.: US 9,562,843 B2
(45) Date of Patent: Feb. 7, 2017

(54) METHOD OF NON-DESTRUCTIVE EVALUATION OF INTERGRANULAR STRESS CORROSION CRACKING (IGSSC) IN STRUCTURAL COMPONENTS MADE OF METAL ALLOYS, AND THE METHOD OF LIFETIME EVALUATION OF THE STRUCTURAL COMPONENTS

(71) Applicant: KOREA ATOMIC ENERGY RESEARCH INSTITUTE, Daejeon (KR)

(72) Inventors: Young-Suk Kim, Daejeon (KR); Sung-Soo Kim, Daejeon (KR); Dae-Whan Kim, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/553,463

(22) Filed: Nov. 25, 2014

(65) Prior Publication Data

US 2016/0161395 A1 Jun. 9, 2016

Related U.S. Application Data

(63) Continuation of application No. PCT/KR2013/005562, filed on Jun. 24, 2013.

(30) Foreign Application Priority Data

Jun. 22, 2012 (KR) ........................ 10-2012-0067503
Jun. 24, 2013 (KR) ........................ 10-2013-0072273

(51) Int. Cl.
*G01N 19/08* (2006.01)
*G01N 17/00* (2006.01)
(Continued)

(52) U.S. Cl.
CPC ............ *G01N 17/006* (2013.01); *G01N 33/20* (2013.01); *G21C 17/00* (2013.01); *G21C 19/207* (2013.01)

(58) Field of Classification Search
CPC ...... G01N 17/006; G01N 33/20; G21C 17/00; G21C 19/207
(Continued)

(56) References Cited

U.S. PATENT DOCUMENTS 5,895,843 A * 4/1999 Taylor ................... H01C 10/46
324/700
5,901,071 A * 5/1999 Sakai ..................... G01N 17/00
148/240

(Continued)

FOREIGN PATENT DOCUMENTS

JP 2001-305113 A 10/2001
JP 2004-340898 A 12/2004

(Continued)

OTHER PUBLICATIONS

A. Marucco, Materials Science and Engineering, A189, 1994, 267-276.

(Continued)

*Primary Examiner* — Max Noori
(74) *Attorney, Agent, or Firm* — Lando & Anastasi, LLP (57) ABSTRACT

A method of non-destructive evaluation of stress corrosion cracking of structural components made of metal alloys, and a method of evaluation of the remaining lifetime of the structural component made of metal alloys are provided, in which a change in properties of the structural components made of metal alloys being used in operating nuclear power plants is measured according to the degree of atomic ordering (or short range ordering) of alloying atoms, and stress corrosion cracking of the structural components made of (Continued)

metal alloys is thus evaluated. The properties to be measured may be one or more selected from a group consisting of hardness, electrical resistivity and thermal conductivity.

12 Claims, 8 Drawing Sheets

(51) Int. Cl.
   *G21C 17/00* (2006.01)
   *G01N 33/20* (2006.01)
   *G21C 19/20* (2006.01)

(58) Field of Classification Search
   USPC .......................................... 73/799, 801, 808
   See application file for complete search history.

(56) References Cited

U.S. PATENT DOCUMENTS

| | | | | |
|---|---|---|---|---|
| 7,214,941 B2* | 5/2007 | Hamelin | ................ | G01N 25/72 |
| | | | | 250/341.1 |
| 8,054,092 B2* | 11/2011 | Fay | ........................ | G01N 17/04 |
| | | | | 324/700 |
| 8,265,884 B2* | 9/2012 | Li | ............................ | G01N 3/42 |
| | | | | 702/33 |
| 8,524,056 B2* | 9/2013 | Ishida | .................... | G01N 17/04 |
| | | | | 204/404 |
| 2004/0195542 A1 | 10/2004 | Bellaiche et al. | | |
| 2012/0132541 A1 | 5/2012 | Kipouros | | |

FOREIGN PATENT DOCUMENTS

| | | |
|---|---|---|
| JP | 2008-032480 A | 2/2008 |
| JP | 2008-086740 A | 4/2008 |
| KR | 2010-0104928 A | 9/2010 |

OTHER PUBLICATIONS

EPRI-1007380: Quantification of yield strength effects on IGSCC in austenitic stainless steels and its implication to IASCC, EPRI, Palo Alto, CA, 2002.
T. Onchi, K. Dohi, N. Soneda, M. Navas, M.L. Castano, Journal of Nuclear Materials, 340 (2005) pp. 219-236.
Young Suk Kim et al., Transactions of the Korean Nuclear Society Autumn Meeting, Jeju Korea, 2010, pp. 1079-1080.
Young Suk Kim et al., Transactions of the Korean Society of Mechanical Engineers, 2012. 02, p. 107-108.

* cited by examiner

METHOD OF NON-DESTRUCTIVE EVALUATION OF INTERGRANULAR STRESS CORROSION CRACKING (IGSSC) IN STRUCTURAL COMPONENTS MADE OF METAL ALLOYS, AND THE METHOD OF LIFETIME EVALUATION OF THE STRUCTURAL COMPONENTS

CROSS-REFERENCE TO RELATED APPLICATIONS

This application is a continuation of International PCT Patent Application Serial No. PCT/KR2013/005562 filed on Jun. 24, 2013 which, in turn, claims the benefit of priority to Korean Patent Application Serial Nos. KR 10-2012-0067503 filed Jun. 22, 2012 and KR 10-2013-0072273 filed Jun. 24, 2013, the entire disclosure of each of which is hereby incorporated herein by reference in its entirety for all purposes.

TECHNICAL FIELD

The invention relates to a non-destructive evaluation of intergranular stress corrosion cracking in structural components made of metal alloys and more particularly, in the structural components of metal alloys of nuclear power plants, and a method for lifetime evaluation of the structural components.

BACKGROUND

All the structural components being used in nuclear power plants that are into contact with coolant water are made from austenitic Fe—Cr—Ni alloys. For example, coolant pipes, core barrels, baffle former bolts are Fe-based austenitic Fe—Cr—Ni alloys such as, for example, 300 series austenitic stainless steels. All these structural components that are into contact with coolant are made from austenitic Fe—Cr—Ni alloys because of their superior resistance to intergranular stress corrosion cracking (IGSCC).

However, when the age of the nuclear power plants exceeds 20 years, austenitic Fe—Cr—Ni alloys turn out to be susceptible particularly to IGSCC in which cracking occurs mainly along grain boundaries. Intergranular (IG) cracking of the structural components in primary water reactor environment is particularly termed 'primary water stress corrosion cracking (PWSCC)' or 'intergranular stress corrosion cracking', while IG cracking in neutron irradiation environment is called 'irradiation assisted stress corrosion cracking (IGSCC)'. The above-mentioned cracking phenomena are often collectively referred to as 'Intergranular (IG) cracking'. As the lifetime of the nuclear power plants is being extended from 40 to 60 years or even beyond, the aging management of nuclear power plants is particularly one of the hot issues to assure the safety of the aged nuclear power plants. From the perspective of the aging management of the nuclear power plants, the core technology particularly relates to the management of IG cracking of the structural components made of austenitic Fe—Cr—Ni alloys which are exposed to primary water.

Unfortunately, no particular technology has been made available so far, in association with the management of IG cracking, albeit either active or proactive, mainly because the intergranular cracking mechanism of austenitic Fe—Cr—Ni alloys has not been fully clarified yet. Instead, the nuclear industry focuses on repair technology of degradated structural components by overlay welding, rather than the proactive management of IG cracking of the structural components itself. Although efforts are made to develop alternative techniques to detect and monitor intergranular cracks in the austenitic Fe—Cr—Ni alloy structural components before propagation of IG cracks into a through-wall crack, IG cracks are too fine to be detected with high reliability by the conventional non-destructive examination techniques. In other words, non-destructive examination techniques to detect and monitor IG cracks of the structural components made of austenitic Fe—Cr—Ni alloys is the core technology for the aging management of nuclear power plants, but no current techniques available so far has fully resolved technical difficulties related to non-destructive examination of IG cracks despite much efforts put forward to date.

Recently, the present inventors showed that austenitic 316L stainless steel, one of the structural materials being used for the structural components of nuclear power plants, had lattice contraction to some extents in reactor operating conditions, due to short range ordering (Young Suk Kim et al., Transactions of the Korean Nuclear Society Autumn Meeting, Jeju Korea, 2010, pp. 1079-1080.)

Accordingly, given the inventors' observation, the inventors proposes a hypothesis that short range order occurring in austenitic Fe—Cr—Ni alloys during plant operation would cause intergranular stress corrosion cracking, and that intergranular stress corrosion cracking susceptibility of the structural components of metal alloys for nuclear power plants can be evaluated non-destructively by measuring variations in their properties accompanying SRO. In short, the inventors attempts to establish the non-destructive evaluation methods to detect and monitor intergranular stress corrosion cracks in the structural components made of austenitic Fe—Cr—Ni alloys and furthermore to assess the remaining lifetime of the structural components made of austenitic Fe—Cr—Ni alloys by accounting for the variations in their properties.

SUMMARY OF THE DISCLOSURE

Technical Problem

The present invention aims to provide non-destructive assessment methods for evaluating intergranular stress corrosion cracking (IGSCC) of the structural components made of metal alloys.

The present invention also aims to provide a method for evaluating the remaining lifetime of the structural components of metal alloys which are degraded by IGSCC.

Technical Solution

In order to achieve the aims described above, the present invention provides non-destructive assessment methods for evaluating intergranular stress corrosion cracking of the structural components made of metal alloys, which include the measurements of changes in the properties of the structural components due to SRO of the solute atoms in the austenitic Fe—Cr—Ni alloys.

Further, the present invention provides a method for evaluating the remaining lifetime of a metal alloy structural component, comprising the steps of: measuring changes in the properties of the structural components due to SRO of the alloying elements (step 1); and evaluating the remaining lifetime of the structural components of metal alloys based on the change in the properties (Step 2).

Advantageous Effects

The present invention is capable of non-destructively detecting and monitoring initiation and growth of very fine IG cracks or stress corrosion cracks which may occur in the structural components made of metal alloys being used in nuclear power plants, which have been otherwise impossible to be detected by the conventional nondestructive examination methods.

Furthermore, it is possible to reliably evaluate the remaining lifetime of the structural component made of metal alloys used in operating nuclear power plants.

Considering that the non-destructive assessment methods for evaluating IG cracking of the structural components and their remaining lifetime can assure the safety of nuclear power plants with life extension, this invention can be used in the effective aging management of the structural components made of metal alloys.

DETAILED DESCRIPTION

[Best Mode]

Hereinafter, the present invention will be explained in greater detail.

The primary objective of the present invention is to provide non-destructive assessment methods for evaluating intergranular stress corrosion cracking (IGSCC) of the structural components made of metal alloys, and, as a detailed countermeasure to implement it, to include a method to determine changes in properties due to the formation of SRO in the structural components made of metal alloys by which non-destructive assessment for intergranular stress corrosion cracking of the structural components made of metal alloys can be made.

The method of the present invention is applicable to degradation evaluation of structural components made of metal alloys such as intergranular stress corrosion cracking of structural components made of metal alloys being used in the entire industry, and more particularly, is applicable to non-destructive assessment of intergranular stress corrosion cracking (IGSCC) of the structural components made of metal alloys in nuclear power plants which are degraded during their reactor operation.

The structural components being used in nuclear power plants is made from austenitic Fe—Cr—Ni alloys, or more specifically, from 300 series austenitic stainless steel, in which all the solute atoms consisting of either Fe-based or Ni-based austenitic alloys, are dissolved in the face-centered cubic (fcc) structure. Meanwhile, the 300 series austenitic stainless steels explained above are widely used in various industrial fields including railways, vehicles, gas and oil pipes, construction exterior materials, bolts or nuts, heat-exchangers, reactor vessels, ships, various plant structural components, as well as nuclear power plants.

Irrespective of whether austenitic Fe—Cr—Ni alloys are either Fe-based or Ni-based alloys, the fcc structure where Fe, Cr and Ni atoms are co-existing can be categorized mainly into three kinds of atomic arrangements.

The first is long-range order (LRO) where the positions of the different species of atoms are not random so that Fe, Cr and Ni atoms are positioned in orderly manner, the second is disorder where the positions of different species of atoms are random and the third is short-range order (SRO) which refers to an intermediate structure that is neither LRO nor DO. From the perspective of thermodynamics, the third one, i.e., SRO would be the most stable structure. Accordingly, austenitic Fe—Cr—Ni alloy has SRO, but with the supply of sufficient heat and mechanical strain energy, SRO gradually transforms into LRO. When the temperature increases beyond a threshold, due to high thermal agitation, SRO transforms into DO in which the arrangements of all solute atoms are completely random.

When austenitic Fe—Cr—Ni alloys are water quenched after solution annealing at and above 950° C. which is above the order-disorder phase transition temperature, all the water-cooled Fe—Cr—Ni alloys would have DO. At reactor operating conditions (300-350° C., 15 MPa), however, atomic ordering occurs in austenitic Fe—Cr—Ni alloys so that it transform from DO to SRO. With the formation of SRO, the number of unlike atoms increases, resulting in lattice contraction due to attractive forces between the unlike atoms, hardness increase and a change in electrical resistivity (A. Marucco, Materials Science and Engineering, A189, 1994, 267-276).

316L stainless steel, one of the representative austenitic Fe—Cr—Ni alloys and also one of the structural component materials, also has lattice contraction due to SRO during operation of the plant. (Young Suk Kim et al., Transactions of the Korean Nuclear Society Autumn Meeting, Jeju Korea, 2010, pp. 1079-1080).

EXPERIMENTAL EXAMPLE 1

Observation on Whether SRO Occurs Under Plant Operating Condition

Figure 1:
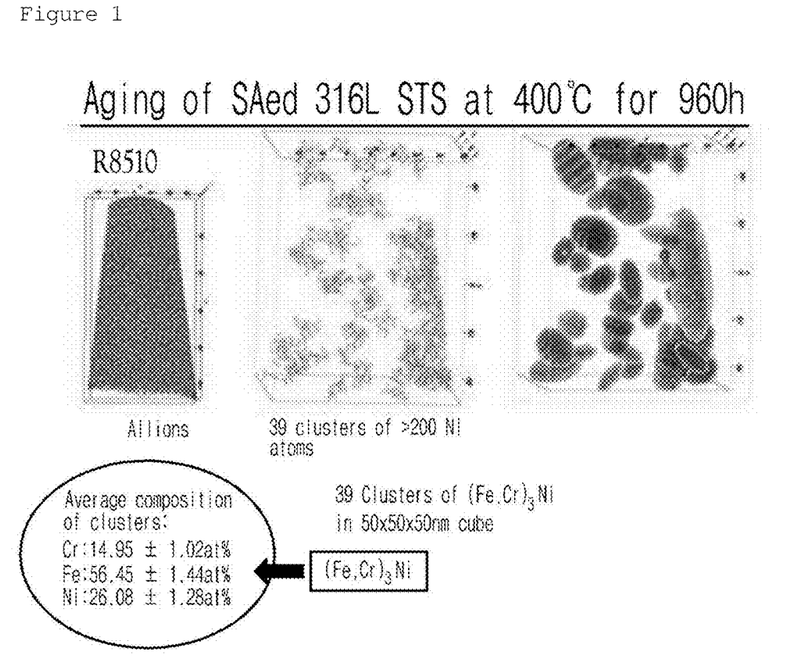
FIG. 1 shows atom probe tomography (APT) analysis of nano-sized particles with short range order formed in solution-annealed 316L stainless steel after aging at 400° C. for 960 h.

In order to demonstrate the formation of SRO in the structural components made of 316L stainless steel in reactor operating conditions, 316L stainless steel given solution annealing at 1100° C., 1 hr followed by water-cooling were aged at 400° C. and then analyzed with atom probe tomography (APT). As shown in FIG. 1, several dozens of (Fe, $Cr)_3Ni$ phase of nano size were observed to form in 316L stainless steel after aging at 400° C. for 960 h. The observation shown in FIG. 1 reveals, for the first time, that atomic ordering occurs in the structural component materials in reactor operating conditions. Thus, this fact suggests that a change in atomic arrangements from DO to SRO due to atomic ordering degrades the mechanical and physical properties of the structural components in reactor operating conditions.

Figure 2:
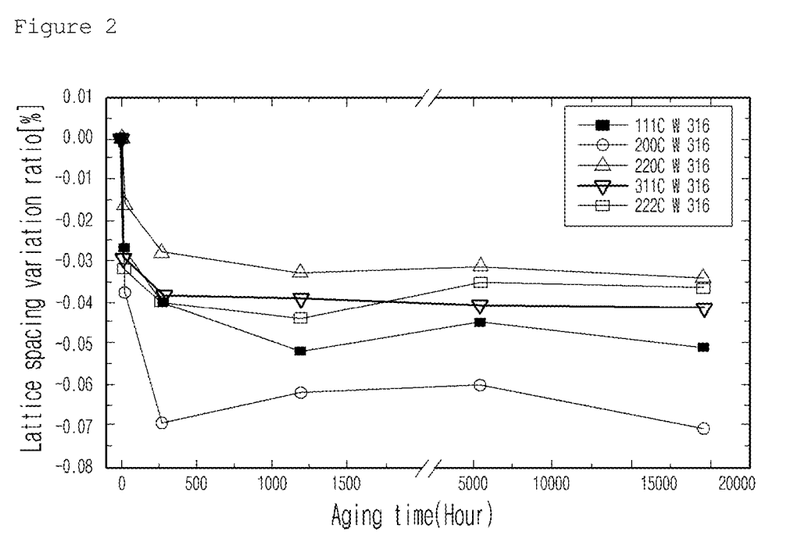
FIG. 2 shows a relative ratio of lattice contraction of crystallographic planes of 316L stainless steel upon aging time at 400° C. which was solution annealed at 1100° C. for 1 h and water quenched followed by 40% cold working.

Considering that atomic ordering occurs by diffusion of atoms, the formation of SRO is enhanced with increasing reactor operating temperature and by moving dislocations by high stresses. To show a correlation between degradation and the formation of SRO in reactor operating conditions, lattice spacing of 40% cold worked 316L stainless steel were determined using neutron diffraction. As shown in FIG. 2, lattice contraction occurred upon aging at 400° C. and the amount of lattice contraction reached 0.07% at the maximum after 20,000 h aging.

Given that the structural components of 316L stainless steel are exposed to plastic deformation due to stress concentration at local areas such as a crack tip and high temperature coolant ranging from 300 to 350° C., the observations shown in FIGS. 1 and 2 demonstrate that SRO is formed in 316L stainless steel in reactor operating conditions, causing lattice contraction to occur and resulting in degradation of 316L stainless steel.

Figure 3:
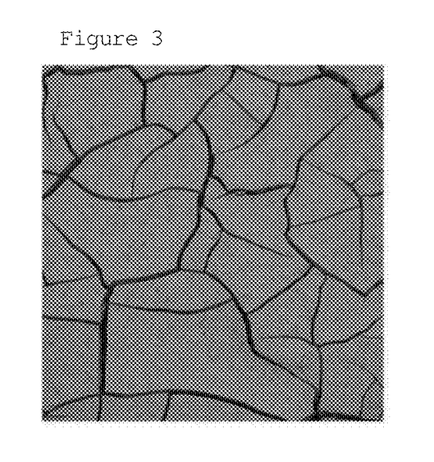
FIG. 3 shows an image of mud cracking occurring due to contraction arising from water evaporation in a drought.

When lattice contraction due to SRO occurs in the grains, the grain boundary when they meet together is subject to tensile stresses so that intergranular cracking occurs. The effect of lattice contraction on material degradation can be found from cracking of mud as shown in FIG. 3 which occurs by contraction due to water evaporation in a drought. Likewise, metals such as 316L stainless steel also suffer from cracking generated particularly at the grain boundary subjected to tensile stresses as a result of lattice contraction due to SRO. Accordingly, in nuclear operating conditions, the more the SRO is formed, the more the amount of lattice contraction becomes, which leads to enhanced IGSCC susceptibility of the structural components made of austenitic Fe—Cr—Ni alloys. On the contrary, if the formation rate of SRO is considerably slow so that no SRO is accompanied in reactor operating conditions, little lattice contraction occurs, leading to no IG cracking. Accordingly, IG cracking of the austenitic stainless steel is an intrinsic phenomenon which occurs in the grains irrespective of grain boundary corrosion or oxidation.

Supportive evidence is provided by the following experimental facts; IG cracking occurred in irradiated 304 stainless steels used in nuclear power plants when slow strain rate tests were conducted in argon atmosphere without exposure to water, where no grain boundary corrosion or oxidation occurred (T. Onchi, K. Dohi, N. Sonata, M. Navas, M. L. Castano, Journal of Nuclear Materials, 340 (2005) pp. 219-236).

In summary, the structural components of nuclear power plants undergo atomic ordering transformation from DO to SRO during operation, leading to lattice contraction in the grains. The higher the degree of lattice contraction becomes, the higher the susceptibility of IG cracking of the structural components. Thus, the degree of IG cracking susceptibility or degradation of the structural components can be evaluated by conducting quantitative analysis of SRO with atom probe tomography (APT). However, considering that the APT analysis is a destructive examination and requires long time and careful sample preparation, it is clear that the APT analysis is inappropriate for non-destructive evaluation of degradation of the structural materials of metal alloys being used in nuclear power plants.

Meanwhile, the formation of SRO causes changes in mechanical or physical properties of all the austenitic Fe—Cr—Ni alloy materials including 316L stainless steel. For example, the formation of SRO increases bond strengths between unlike atoms, resulting in an increase in hardness and thermal conductivity and a change in electrical resistivity. (A. Marucco, Materials Science and Engineering, A189, 1994, 267-276).

Therefore, it is possible to quantitatively and non-destructively evaluate the degree of SRO formed in the structural component materials by evaluating changes in physical properties such as hardness or electrical resistivity, thermal conductivity and etc.

For proactive management of degraded structural components of nuclear power plants, many attempts have been made to examine and measure the presence and size of fine IG cracks by numerous non-destructive examination techniques, but none have been successful. Indeed, it is very difficult to detect fine IG cracks present in the bulk of the structural components with the conventional non-destructive methods.

Compared to the conventional methods, the non-destructive evaluation method according to the present invention is characterized by the evaluation of intergranular cracking susceptibility of the structural component materials by measuring changes in their mechanical or physical properties due to the formation of SRO, based on the initial experimental data that indicates that SRO occurs within the structural component materials during operation (see FIGS. 1 and 2) and that the structural component materials undergo changes in their mechanical and physical properties due to SRO. In other words, since the formation of SRO causes not only lattice contraction, but also changes in properties such as increased hardness and changes in thermal conductivity and electrical resistivity, it is possible to evaluate the degree of intergranular cracking susceptibility of 316L stainless steel by tracking the changes in the properties.

According to a method for evaluating intergranular stress corrosion cracking of structural components made of metal alloys according to the embodiment of the present invention, the properties, which are subject to change due to atomic ordering in the structural components made of metal alloys during reactor operation, may include hardness, thermal conductivity, or electrical resistivity, and the main idea is to evaluate the degree of SRO and then intergranular stress corrosion cracking susceptibility by measuring changes in the properties of the structural components made of metal alloys.

The hardness may be measured by a nano indentation method. Additionally, electrical resistivity and thermal conductivity may also be measured by a four point probe method and by a transient plane source measurement or laser flash method, respectively.

The method for evaluating the presence and degree of intergranular stress corrosion cracking may be performed in the following manner.

For example, based on assumption that the initial hardness of the austenitic stainless steel of the nuclear structural components is 170 Hv by Vickers hardness test, and that a critical hardness at which intergranular cracking initiates in a austenitic stainless steel used in the nuclear structural component is, for example, 230-250 Hv, if there are empirical or experimental values indicative of the rate of hardness increase for the austenitic stainless steel over operation time, it is possible to evaluate the intergranular cracking susceptibility and also the lifetime of the nuclear structural component, based on the hardness of a structural component that is measured at a specific time.

It is another object of the present invention to provide a method for evaluating the remaining lifetime of the structural components of metal alloys against intergranular stress corrosion cracking thereof.

According to the present invention, a method for evaluating the remaining lifetime of structural components made of metal alloys is provided, which may include the steps of:

measuring changes in the property of structural components made of metal alloys in accordance with an ordering of alloying elements (step 1); and evaluating the remaining lifetime of the structural components of metal alloys based on the change in the properties (Step 2).

For a method for evaluating the remaining lifetime of the structural components made of metal alloys against intergranular stress corrosion cracking according to an embodiment of the present invention, step 1 may be performed in the manner of the non-destructive evaluation method as explained above.

Step 2, which is the step of evaluating the remaining lifetime of the structural components of metal alloys based on the change in the properties (Step 2).

To be specific, a correlation between a change in properties of the structural components made of metal alloys and initiation and crack growth rate of intergranular cracking both of which are dictated by the degree of SRO formed may be obtained in advance, and then the remaining lifetime may be determined by calculating the change ratio of the properties of the structural components made of metal alloys with operational time.

EXPERIMENTAL EXAMPLE 2

Investigation on if IG Cracking Occurs by the Formation of SRO in Structural Components Made of Metal Alloys in Reactor Operating Conditions To investigate if SRO occurring in the structural component materials in reactor operating conditions causes intergranular cracking of the structural components of nuclear power plants due to lattice contraction, an ingot of $Fe_3Ni$ composition was prepared, which has the same alloying composition as that of the SRO phase-$(Fe,Cr)_3Ni$ as illustrated in FIG. 1. The $Fe_3Ni$ ingot was made by vacuum induction melting and hot rolled into plates and solution annealed at 1050° C. for 1 h followed by cooling by two ways: water quenching (WQ) and furnace cooling (FC). Thus, the WQ sample has DO structure and the FC sample has SRO structure due to atomic ordering accompanied during slow cooling.

Figure 4A:
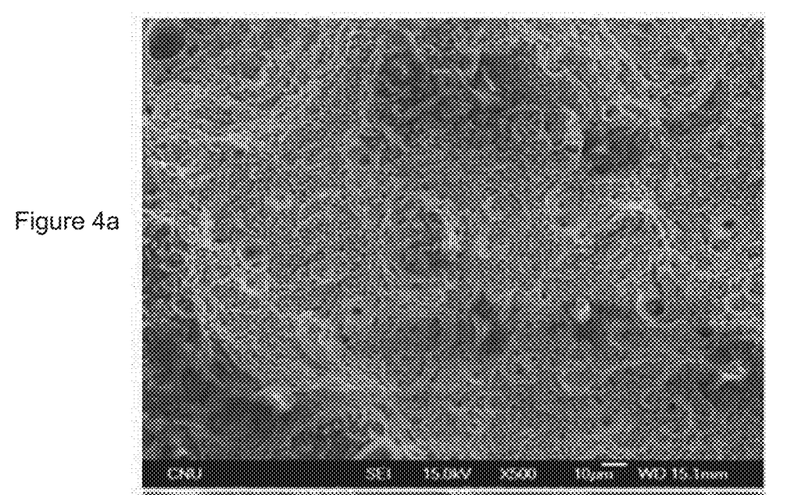
FIGS. 4(a) and 4(b) shows SEM images of fractures surfaces of the (a) water quenched and (b) furnace cooled $Fe_3Ni$ upon tensile tests at room temperature. The ingots whose nominal composition corresponds to $Fe_3Ni$ were made by vacuum induction melting, hot rolled and then solution annealed at 1050° C. for 1 h.
Figure 4B:
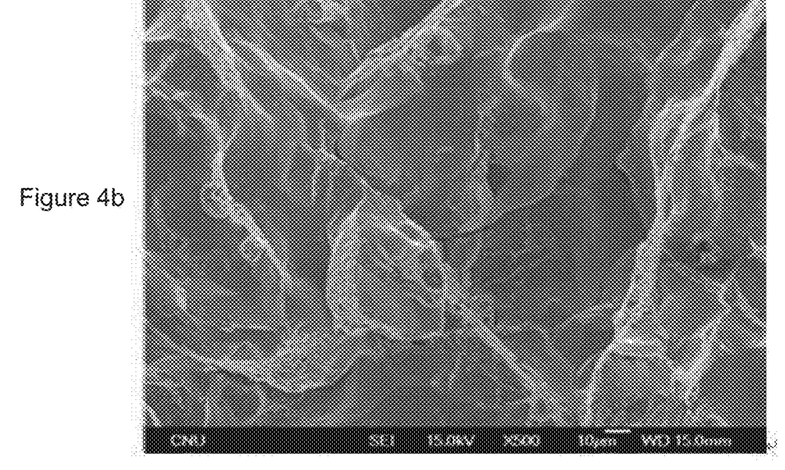

Tensile tests were conducted at room temperature in order to demonstrate the effects of atomic arrangements such as DO and SRO on intergranular cracking. As shown in FIG. 4, the WQ-$Fe_3Ni$ sample with DO had dimple ductile fracture, while the FC—$Fe_3Ni$ sample with SRO showed brittle fracture by intergranular cracking. The observation of FIG. 4 shows that the formation of SRO causes lattice contraction as shown in FIG. 2, resulting in IG cracking with brittle fracture during tensile tests at room temperature.

EXPERIMENTAL EXAMPLE 3

Investigation on Hardness Increase Due to SRO Occurring in Reactor Operating Conditions 300 series austenitic stainless steels forms SRO in reactor operating conditions as shown in FIG. 1, and lattice contraction due to SRO degradates austenitic stainless steels with intergranular cracking, as confirmed in the tensile tests at room temperature on furnace-cooled $Fe_3Ni$ as shown in FIG. 4.

Figure 5:
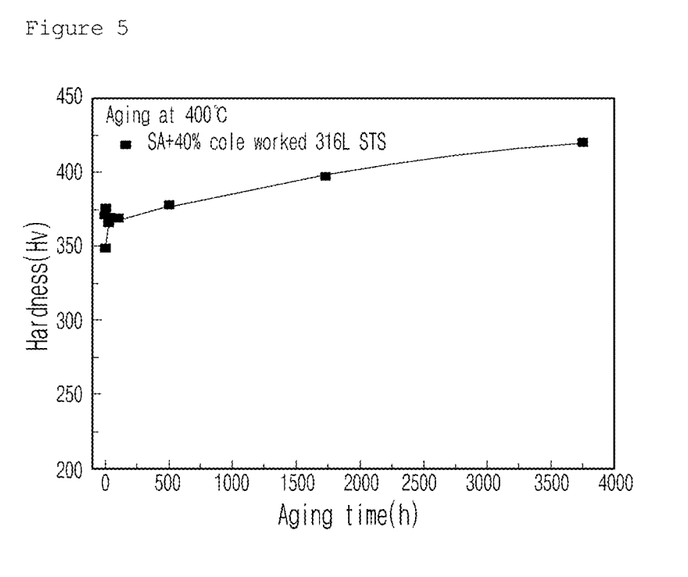
FIG. 5 shows hardness increase of 40% cold worked 316L stainless steel upon aging at 400° C.

As one of non-destructive parameters for the evaluation of degradation of the structural component materials, to confirm if the structural components made of metal alloys of nuclear power plants show hardness increase, the hardness of 316L stainless steel given solution annealing and 40% cold working were determined with aging time at 400° C. whew a change in atomic arrangements of austenitic stainless steels in reactor operating conditions can be simulated. As shown in FIG. 5, the hardness of 40% cold worked 316L stainless steel increased with aging time from 350 Hv to 400 Hv. Given that the SRO phase formed is harder than the matrix, the observation in FIG. 5 shows that the formation of SRO during reactor operation increases with operational time, leading to an increase in hardness of 300 series austenitic stainless steels in proportion to the degree of SRO formed.

In general, aging is recognized to decrease the hardness of materials. Accordingly, the above result that the hardness of 316L stainless steel has increased with aging time in simulated reactor operating conditions indicates the formation of SRO and thereby a change in properties of 316L stainless steel during reactor operation. Additionally, considering that aging degradation, i.e., intergranular cracking increases in accordance with nuclear plant operation time, it is possible to perform non-destructive evaluation on intergranular cracking based on the changes in properties, such as hardness increase, or the like, which occur due to the formation of SRO.

Accordingly, the result of FIG. 5 indicates that, by non-destructively detecting hardness increase of the structural components made of metal alloys, it is possible to evaluate the degree of SRO occurring in the nuclear structural component and thus to non-destructively evaluate the intergranular cracking susceptibility and the remaining lifetime of the structural components made of metal alloys. Further, considering the result of FIG. 4 that the formation of SRO causes intergranular cracking of the structural components made of metal alloys, the result of FIG. 5 is in agreement with the reported result which explains that the intergranular cracking susceptibility of the nuclear structural components including austenitic stainless steel increases in proportion to the amount of cold-working. (EPRI-1007380: Quantification of yield strength effects on IGSCC in austenitic stainless steels and its implication to IASCC, EPRI, Palo Alto, Calif., 2002).

EXPERIMENTAL EXAMPLE 4

Figure 7:
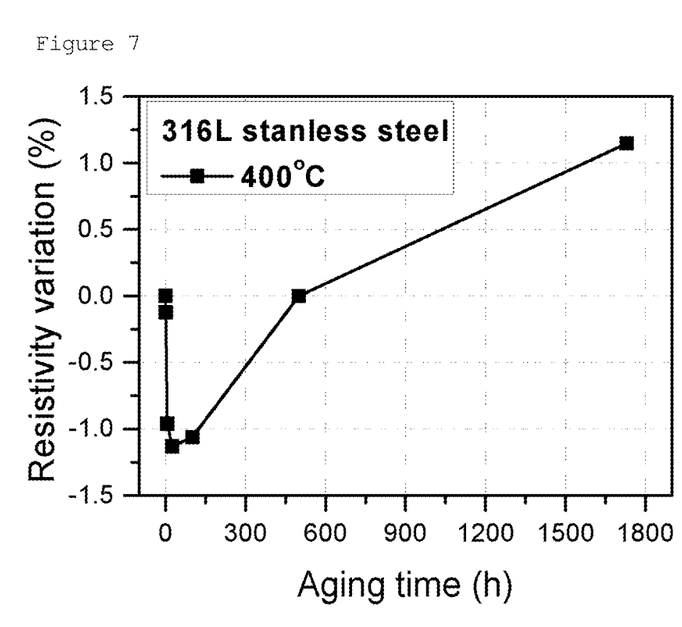
FIG. 7 shows a ratio of electrical resistivity of 316L stainless steel with aging time at 400° C. when compared to that of the unaged one.

Investigation on a Change in Electrical Resistivity Due to SRO Occurring in Reactor Operating Conditions The 300 series austenitic stainless steels under nuclear power plant operating conditions forms SRO, and the lattice contraction by SRO degradates the austenitic stainless steel with intergranular cracking, as is confirmed in the test on whether SRO causes intergranular cracking, as shown in Experimental Example 2. Accordingly, it is possible to evaluate the intergranular crack susceptibility of the austenitic stainless steel using quantitative and direct method of measuring the degree of SRO being accompanied with operational time. The problem is that while it is possible to observe the SRO occurring in the austenitic stainless steels by destructive test, direct and non-destructive measurements are not possible. Accordingly, the following experiment was conducted to show that the degree of SRO can be evaluated by detecting a change in electrical resistivity of the austenitic stainless steels. Samples with various electrical resistivities were made by cold working and aging of 316L stainless steel in conditions to simulate microstructural changes in the structural components made of metal alloys in reactor operating conditions. To be more specific, the electrical resistivity of 40% cold worked 316L stainless steel was determined with aging time at 400° C. FIG. 7 shows the ratio of electrical resistivity of 316L stainless steel after aging when compared to that of the unaged one ((electrical resistivity after aging−electrical resistivity before aging)/ (electrical resistivity before aging)) as a function of aging time. The electrical resistivity can be measured by 4 point probe measurement.

Referring to FIG. 7, the electrical resistivity of 316L stainless steel when compared to that of the unaged one rapidly decreased upon aging at 400° C., i.e., under a simulated condition of nuclear power plant operation, and then increased linearly as SRO is formed. This shows that it is possible to non-destructively evaluate the intergranular cracking susceptibility of the stainless steel due to SRO, because it is possible to quantitatively evaluate the degree of SRO occurring in the stainless steel by tracking a change in the electrical resistivity of the 316L stainless steel during operation of nuclear power plants.

EXPERIMENTAL EXAMPLE 5

Figure 8:
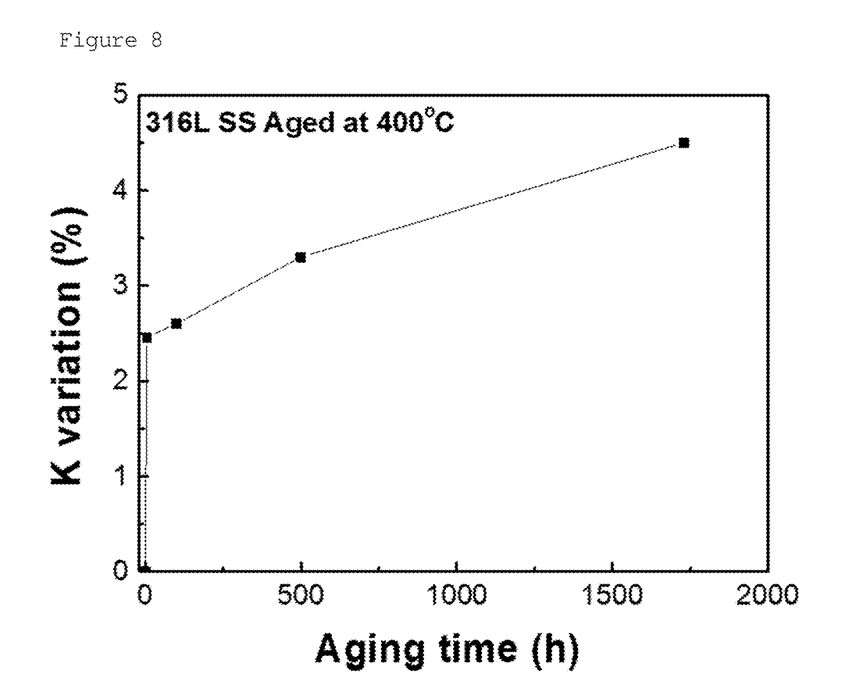
FIG. 8 is a ratio of thermal conductivity at room temperature of 316L stainless steel with aging time at 400° C. when compared to that of the unaged one.

Investigation on Change in Thermal Conductivity Due to SRO Occurrence Under Nuclear Power Plant Operation Condition The 300 series austenitic stainless steels under nuclear power plant operation temperature condition forms SRO, and the lattice contraction occurred by SRO degradates the austenitic stainless steel by intergranular cracking, as is confirmed in the test results of FIG. 4. Accordingly, it is possible to evaluate the intergranular crack susceptibility of the austenitic stainless steel using quantitative and direct method of measuring a degree of SRO as occurred. The problem is that while it is possible to observe the SRO occurring on the base of the austenitic stainless steel by destructive test, direct, non-destructive measurement is not possible. Accordingly, the following experiment was conducted to investigate if it is possible to evaluate the degree of SRO occurring in the structural components made of metal alloys by tracking changes in their thermal conductivity. Samples with various thermal conductivities were made by cold working and aging of 316L stainless steel in conditions to simulate microstructural changes in the structural components made of metal alloys in reactor operating conditions. To be more specific, the thermal conductivity of 40% cold worked 316L stainless steel was determined with aging time at 400° C. FIG. 8 shows the ratio of thermal conductivity of 316L stainless steel after aging when compared to before aging ((thermal conductivity after aging− thermal conductivity before aging)/(thermal conductivity before aging)). The thermal conductivity can be measured by transient plane source measurement or laser flash method.

Referring to FIG. 8, as the degree of SRO increased, the thermal conductivity at room temperature of 316L stainless steel when compared to that of the unaged one increased with increasing aging time at 400° C. i.e., under a simulated condition of a nuclear power plant operation. For example, upon aging at 400° C., the thermal conductivity after aging when compared to that before aging increased sharply at the beginning and increased linearly after that. This shows that it is possible to non-destructively evaluate the intergranular cracking susceptibility of the stainless steel due to SRO, because it is possible to quantitatively evaluate the degree of SRO occurring in the stainless steel by tracking a change in thermal conductivity of the 316L stainless steel during operation of nuclear power plants.

That is, SRO is the factor that causes intergranular cracking, which are characteristics of degraded nuclear structural components, and it is possible to evaluate the degree of degradation of the nuclear materials and lifetime thereof with a non-destructive manner by evaluating changes in property of the nuclear structural component such as, for example, hardness, electrical resistivity or thermal conductivity, which occur due to the formation of SRO.

EXAMPLE 1

Figure 6:
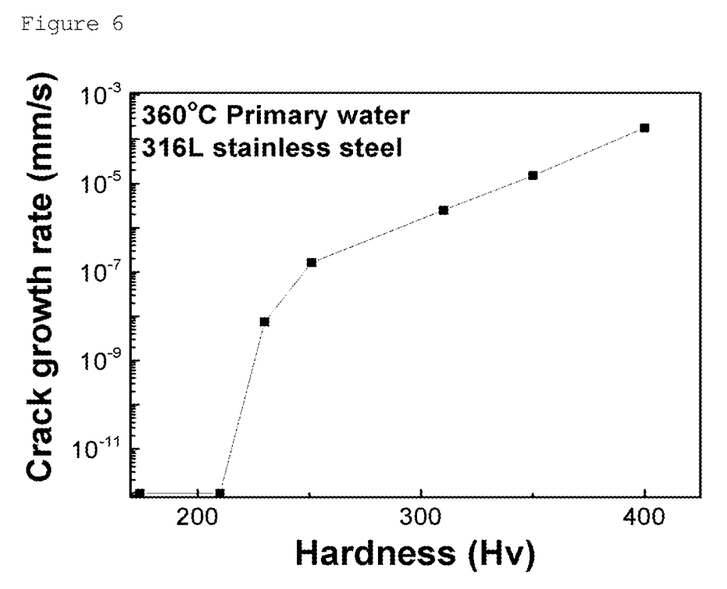
FIG. 6 shows crack growth rate of 316L stainless steel with hardness in simulated primary water of 360° C.

Investigation on Initiation and Crack Growth Rate of Intergranular Cracking of Austenitic Stainless Steel with their Hardness in Reactor Operating Conditions To show if hardness increase of 316L stainless steel enhances the intergranular cracking susceptibility and crack growth rate of structural components in reactor operating conditions, the hardness of the solution-annealed (SA) 316L stainless steel was changed by cold working and long-term aging at 400° C. The hardness of the SA 316L stainless steel was increased from 174 Hv to 350 Hv by changing the amount of cold working and it was further increased from 350 Hv to 400 Hv by change aging time at 400° C. following 40% cold working, as shown in FIG. 5. The SA 316L stainless steels with different hardness were exposed to simulated primary water of 360° C. (2 ppm Li, 500 ppm B, $O_2$<5 ppb) using compact tension specimens with 0.5 T (12.7 mm) or 1 T (25.4 mm) thickness to detect crack initiation and crack growth rate. As shown in FIG. 6, the SA 316L stainless steel equal to or lower than 210 Hv showed no initiation of IG cracking. However, the SA 316L stainless steel with the hardness increased to 230 Hv showed initiation of IG cracking, and once IG cracking occurred, the crack growth rate of SA 316L stainless steel increased in almost linear proportion to the hardness. The results of FIG. 6 reveal that intergranular cracking is initiated in SA 316L stainless steel only when the hardness of the 316L stainless steel increases to above 230 Hv. Furthermore, the results also indicate that the rate of intergranular cracking of the 316L stainless steel increases in proportion to the hardness. Accordingly, considering that IG cracking was initiated in SA 316L stainless steel whose hardness reaches a threshold value, i.e., 230 Hv, when the hardness of the stainless steel in operation reaches a threshold hardness, i.e., 230 Hv, it is possible to quantitatively evaluate the PWSCC susceptibility of the austenitic stainless steel by tracking changes in the hardness, and also possible to evaluate the remaining lifetime of the stainless steel by quantitatively evaluating the growth time between initiation of intergranular cracking until penetration defect occurs, based on a correlation formula on hardness-based crack growth rate of IG cracking. That is, it is possible to measure the hardness of the austenitic stainless steel over operational time, and using a previously-determined relationship of hardness-based cracking growth rate, to non-destructively evaluate the degree of IG cracking susceptibility and the remaining lifetime, accordingly.

Based on the above test results, it is confirmed that SRO is accompanied in reactor operating conditions, and hardness increase and lattice contraction due to SRO enhances the intergranular cracking susceptibility as well as crack growth rate. Accordingly, the increase of hardness due to SRO is applicable as an index to evaluate the degree of intergranular cracking susceptibility. Since the degree of SRO can be non-destructively evaluated based on hardness increase, etc., this in turn indicates that intergranular cracking susceptibility of structural components made of metal alloys can be non-destructively evaluated with the hardness increase, etc.

EXAMPLE 2

Investigation on Initiation and Crack Growth Rate of Intergranular Cracking of Austenitic Stainless Steel with a Change in Electrical Resistivity in Reactor Operating Conditions To show if a change in electrical resistivity of the 316L stainless steel affects the intergranular cracking susceptibility and crack growth rate of structural components in reactor operating conditions, electrical resistivity of the solution-annealed (SA) 316L stainless steel was changed by cold working and long-term aging at 400° C. With aging time, the ratio of electrical resistivity of the SA 316L stainless steel when compared to that of the unaged one decreased rapidly and then increased with aging time, as shown in FIG. 7. The transition point corresponding to onset of an increase in electrical resistivity ratio occurs due to onset of SRO formation.

The SA 316L stainless steels with different electrical resistivity were exposed to simulated primary water of 360° C. (2 ppm Li, 500 ppm B, $O_2$<5 ppb) using compact tension specimens with 0.5 T (12.7 mm) or 1 T (25.4 mm) thickness to detect crack initiation and crack growth rate. When electrical resistivity ratio of SA 316L stainless steel showed the minimum value or a transition point above which it increased with aging time, initiation of IG cracking occurred and then crack growth rate of SA 316L stainless steel increased almost linearly with electrical resistivity.

Based on the above test results, it is confirmed that initiation of IG cracking occurs when electrical resistivity ratio of SA 316L stainless steel reached a minimum value or a transition point, corresponding to onset of the formation of SRO. Accordingly, a change in electrical resistivity ratio due to SRO is applicable as an index to the quantitative evaluation of IG cracking susceptibility of austenitic stainless steels. Furthermore, the remaining lifetime of the cracked austenitic stainless steels can be evaluated by quantitative assessment of the time required for an IG crack to grow to a through-wall crack using a predetermined correlation between electrical resistivity ratio and crack growth rate of structural component materials. Since the degree of SRO can be non-destructively evaluated based on a change in electrical resistivity ratio, etc., this in turn indicates that intergranular cracking susceptibility of structural components made of metal alloys can be non-destructively evaluated with a change in electrical resistivity ratio, etc.

EXAMPLE 3

Investigation on Initiation and Crack Growth Rate of Intergranular Cracking of Austenitic Stainless Steel with a Change in Thermal Conductivity in Reactor Operating Conditions To show if a change in thermal conductivity of solution annealed (SA) 316L stainless steel enhances the intergranular cracking susceptibility and crack growth rate of structural components in reactor operating conditions, thermal conductivity of the solution-annealed (SA) 316L stainless steel was changed by cold working and long-term aging at 400° C. With aging time, thermal conductivity ratio of SA 316L stainless steel when compared to that of the unaged one increased rapidly and then showed a linear increase with aging time, as shown in FIG. 8.

The SA 316L stainless steels with different thermal conductivity were exposed to simulated primary water of 360° C. (2 ppm Li, 500 ppm B, $O_2$<5 ppb) using compact tension specimens with 0.5 T (12.7 mm) or 1 T (25.4 mm) thickness to detect crack initiation and crack growth rate. When an increased ratio of thermal conductivity of SA 316L stainless steel reached 2.6%, initiation of IG cracking occurred and then crack growth rate of SA 316L stainless steel increased almost linearly with increasing thermal conductivity ratio.

Based on the above test results, it is confirmed that initiation of IG cracking occurs when an increased ratio of thermal conductivity of SA 316L stainless steel due to SRO reached a critical value of 2.6%. Accordingly, a change in thermal conductivity due to SRO is applicable as an index to the quantitative evaluation of IG cracking susceptibility of austenitic stainless steels. Furthermore, the remaining lifetime of the cracked austenitic stainless steels can be evaluated by quantitative assessment of the time required for an IG crack to grow to a through-wall crack using a predetermined correlation between an increased ratio of thermal conductivity and crack growth rate of structural component materials. Since the degree of SRO can be non-destructively evaluated based on a change in thermal conductivity, etc., this in turn indicates that intergranular cracking susceptibility of structural components made of metal alloys can be non-destructively evaluated with a change in thermal conductivity, etc.

The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims.

What is claimed is:
1. A method of evaluating a remaining lifetime of structural components of metal alloys, the method comprising the steps of:
   measuring a change in properties of the structural components of metal alloys based on a degree of short range ordering (SRO); and
   evaluating the remaining lifetime of the structural components of the metal alloys based on the change in the properties.
2. The method as set forth in claim 1, wherein the structural components of metal alloys are for use in nuclear power plants.
3. The method as set forth in claim 1, wherein SRO occurs in reactor operating conditions.

4. The method as set forth in claim 1, wherein the structural components of metal alloys are in contact with a coolant in nuclear power plants.

5. The method as set forth in claim 2, wherein the structural components of metal alloys for use in nuclear power plants are made from austenitic Fe—Cr—Ni alloys.

6. The method as set forth in claim 1, wherein the structural components of metal alloys are selected from a group consisting of coolant pipes, baffles, core barrels, instrumentation guide tubes, holddown springs, upper core supports, lower core supports, upper guide tube structures, core shrouds, bolts and pins.

7. The method as set forth in claim 4, comprising evaluating stress corrosion cracking by evaluating intergranular cracking susceptibility based on a quantitative determination of the degree of SRO.

8. The method as set forth in claim 1, wherein the properties are selected from a group consisting of hardness, thermal conductivity, and electrical resistivity.

9. The method as set forth in claim 8, wherein the hardness is measured using a nano indentation method.

10. The method as set forth in claim 8, wherein the thermal conductivity is measured in a transient plane source measurement or laser flash method.

11. The method as set forth in claim 8, wherein the electrical resistivity is measured in a four point probe measurement method.

12. The method as set forth in claim 5, wherein the structural components of metal alloys are made from 300 series austenitic stainless steels.

* * * * *

UNITED STATES PATENT AND TRADEMARK OFFICE
CERTIFICATE OF CORRECTION

PATENT NO. : 9,562,843 B2
APPLICATION NO. : 14/553463
DATED : February 7, 2017
INVENTOR(S) : Young-Suk Kim et al.

It is certified that error appears in the above-identified patent and that said Letters Patent is hereby corrected as shown below:

In the Specification

At Column 1, Line number 50, delete "IGSCC" and insert -- IASCC --

Signed and Sealed this
Thirtieth Day of May, 2017

Michelle K. Lee
*Director of the United States Patent and Trademark Office*